United States Patent [19]

Ueda et al.

[11] Patent Number: 4,563,455
[45] Date of Patent: Jan. 7, 1986

[54] ANTIULCER FUSED IMIDAZOLE COMPOUNDS

[75] Inventors: Ikuo Ueda, Uenohagashi; Masayuki Kato, Minoo; Masanobu Nagano, Suita; Atsushi Akahane, Ikeda, all of Japan

[73] Assignee: Fujisawa Pharmaceutical Co., Ltd., Osaka, Japan

[21] Appl. No.: 587,981

[22] Filed: Mar. 9, 1984

[30] Foreign Application Priority Data

Mar. 22, 1983 [GB] United Kingdom ............... 8307865

[51] Int. Cl.$^4$ ............... A61K 31/53; C07D 403/06; C07D 401/06; C07D 417/06
[52] U.S. Cl. ................... 514/241; 514/245; 514/338; 514/359; 514/367; 514/381; 514/383; 514/394; 544/180; 544/212; 544/215; 546/271; 548/159; 548/251; 548/252; 548/254; 548/255; 548/262; 548/266; 548/327
[58] Field of Search ............... 548/327, 251, 252, 254, 548/255, 262, 266, 159; 544/180, 212, 215; 546/271; 514/338, 381, 367, 383, 359, 394, 245, 241

[56] References Cited

U.S. PATENT DOCUMENTS 3,897,432 7/1975 Shen et al. ............... 548/327 X

FOREIGN PATENT DOCUMENTS 455104 5/1975 U.S.S.R. ............... 548/327

OTHER PUBLICATIONS

*Chemical Abstracts*, 72:111365d (1970) [Kolodyazhnaya, S. et al., *Khim. Geterotsikl. Soedin.*, 1970, (2), 238–244].

Primary Examiner—Richard A. Schwartz
Attorney, Agent, or Firm—Oblon, Fisher, Spivak, McClelland & Maier

[57] ABSTRACT

New fused imidazole compounds of the formula:

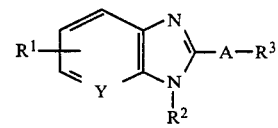

wherein
A is lower alkylene,
$R^1$ is hydrogen, lower alkyl, lower alkoxy or halogen,
$R^2$ is hydrogen, lower alkyl, cyclo(lower)alkyl, pyridyl, ar(lower)alkyl which may be substituted with halogen, or aryl which may be substituted with lower alkyl, lower alkoxy, hydroxy or halogen,
$R^3$ is N-containing unsaturated heterocyclic group which may be substituted with lower alkyl or amino, and
Y is =C— or =N—, and pharmaceutically acceptable salts thereof, and processes for preparation thereof and pharmaceutical composition comprising the same.

These derivatives and salts thereof are useful as antiulcer agents.

7 Claims, No Drawings

ANTIULCER FUSED IMIDAZOLE COMPOUNDS

The present invention relates to novel fused imidazole compounds and pharmaceutically acceptable salts thereof. More particularly, it relates to novel fused imidazole compounds and pharmaceutically acceptable salts thereof which have inhibitory activity on ulcer, to process for preparation thereof, to pharmaceutical composition comprising the same, and to method of using the same therapeutically in the treatment of ulcer in human being and animals.

Accordingly, one object of this invention is to provide novel fused imidazole compounds and pharmaceutically acceptable salts thereof, which are useful as a medicine for ulcer.

Another object of this invention is to provide process for preparation of said fused imidazole compounds and pharmaceutically acceptable salts thereof.

A further object of this invention is to provide pharmaceutical composition comprising, as an active ingredient, said fused imidazole compound or its pharmaceutically acceptable salt.

Still further object of this invention is to provide method of using said fused imidazole compound or its pharmaceutically acceptable salt in the treatment of ulcers in human being and animals.

The fused imidazole compounds of this invention are novel and can be represented by the following general formula (I):

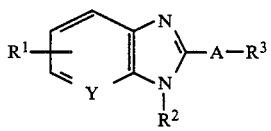

(I)

wherein
  A is lower alkylene,
  $R^1$ is hydrogen, lower alkyl, lower alkoxy or halogen,
  $R^2$ is hydrogen, lower alkyl, cyclo(lower)alkyl, pyridyl, ar(lower)alkyl which may be substituted with halogen, or aryl which may be substituted with lower alkyl, lower alkoxy, hydroxy or halogen,
  $R^3$ is N-containing unsaturated heterocyclic group which may be substituted with lower alkyl or amino, and
  Y is =C— or =N—. A suitable subdefinition for $R^1$ is hydrogen or lower alkoxy, and a suitable subdefinition for $R^2$ is hydrogen, lower alkyl, ar(lower)alkyl which may be substituted with halogen, or aryl which may be substituted with lower alkyl, lower alkoxy or halogen.

According to this invention, the object compounds (I) and their salts can be prepared by the following processes.

Process 1

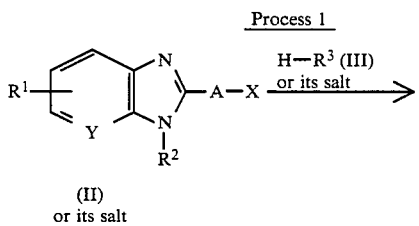

(II)
or its salt

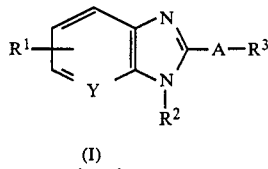

(I)
or its salt

Process 2

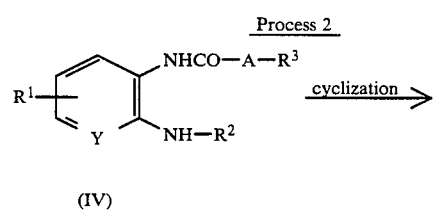

(IV)
or its salt

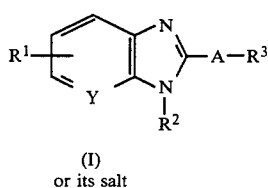

(I)
or its salt

Process 3

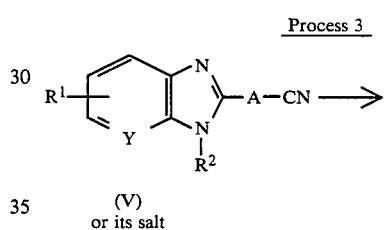

(V)
or its salt

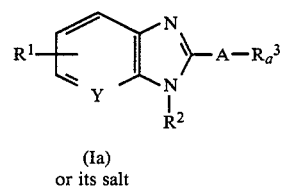

(Ia)
or its salt wherein
  $R^1$, $R^2$, $R^3$, A and Y are each as defined above,
  $R_a^3$, 1H-tetrazol-5-yl or 2,4-diamino-1,3,5-triazin-6-yl, and X is an acid residue.

In the above and subsequent description of the present specification, suitable examples and illustrations for the various definitions to be included within the scope of the invention are explained in detail as follows:

The term "lower" is intended to mean 1 to 6 carbon atom(s) unless otherwise indicated.

Suitable examples of lower alkylene for A may be methylene, ethylene, ethylidene, propylene, trimethylene, tetramethylene, pentamethylene, hexamethylene or the like.

Suitable examples of lower alkyl for $R^1$ and $R^2$ may be a straight or branched one such as methyl, ethyl, propyl, isopropyl, butyl, isobutyl, tert-butyl, pentyl, hexyl or the like.

Suitable examples of lower alkoxy for $R^1$ may be methoxy, ethoxy, propoxy, isopropoxy, butoxy, isobutoxy, tert-butoxy, pentyloxy, hexyloxy or the like.

Suitable examples of halogen for $R^1$ may be chlorine, bromine, iodine or fluorine.

Suitable examples of cyclo(lower)alkyl for $R^2$ may be cyclopropyl, cyclobutyl, cyclopentyl, cyclohexyl or the like.

Suitable examples of ar(lower)alkyl for $R^2$ may be benzyl, phenethyl, 3-phenylpropyl, benzhydryl, trityl or the like. Said ar(lower)alkyl group may be substituted with the aforementioned halogen, and suitable examples of the halogenated ar(lower)alkyl may be 2-chlorobenzyl, 4-chlorobenzyl, 4-bromobenzyl, 4-iodobenzyl, 4-fluorobenzyl, 2,4-dichlorobenzyl, 2-bromo-4-chlorobenzyl, 4-chlorophenethyl, 3-(4-chlorophenyl)propyl, 4-chloro-benzhydryl, 4,4'-dichlorobenzhydryl or the like.

Suitable examples of aryl for $R^2$ may be phenyl, naphthyl or the like. Said aryl group may have one or more substituent(s) selected from the groups consisting of hydroxy and the aforementioned lower alkyl, lower alkoxy and halogen.

Suitable examples of aryl group having such substituent(s) may be lower alkyl substituted aryl [e.g. tolyl, xylyl, 4-ethylphenyl, 4-methyl-1-naphthyl, etc.], lower alkoxy substituted aryl [e.g. 4-methoxyphenyl, 3,4-dimethoxyphenyl, 6-ethoxyphenyl, 5-methoxy-1-naphthyl, etc.], halogenated aryl [e.g. 3-chlorophenyl, 4-chlorophenyl, 2,4-dichlorophenyl, 8-chloro-2-naphthyl, etc.], hydroxy substituted aryl [e.g. 2-hydroxyphenyl, 4-hydroxyphenyl, 1-hydroxy-2-naphthyl, etc.]or the like.

Suitable examples of N-containing unsaturated heterocyclic group for $R^3$ may be unsaturated 3- to 9-membered (preferably 5- to 6-membered) mono or polycyclic heterocyclic group containing 1 to 4 nitrogen atom(s) such as imidazolyl, pyrazolyl, triazolyl [e.g. 1H-1,2,3-triazolyl, 1H-1,2,4-triazolyl, 2H-1,2,3-triazolyl, 4H-1,2,4-triazolyl, etc.], tetrazolyl [e.g. 1H-tetrazolyl, 2H-tetrazolyl, etc.], pyridyl [e.g. 2-pyridyl, 3-pyridyl or 4-pyridyl], pyrimidinyl, pyrazinyl, pyridazinyl, 1,3,5-triazinyl, 2-oxo-benzothiazolinyl, or the like. A suitable subdefinition for $R^3$ is imidazolyl, pridyl, triazolyl, tetrazolyl, 1,3,5-triazinyl and 2-oxo-benzothiazolinyl, when Y is =C—.

The above-mentioned heterocyclic groups may be substituted with the aforementioned lower alkyl group(s) or amino group(s). Suitable examples of the heterocyclic group having such substituent(s) may be imidazolyl [e.g. 2-methylimidazol-1-yl, 4-methylimidazol-1-yl, 5-methylimidazol-1-yl, 4-ethylimidazol-1-yl, 4-hexylimidazol-1-yl, etc.], pyrazolyl [e.g. 3-methylpyrazol-1-yl, 4-methylpyrazol-1-yl, etc.], triazolyl [e.g. 4-methyl-1H-1,2,3-triazol-1-yl, 3-methyl-1H-1,2,4-triazol-1-yl, 4-methyl-2H-1,2,3-triazol-2-yl, 3-methyl-4H-1,2,4-triazol-4-yl, etc.], tetrazolyl [e.g. 5-methyl-1H-tetrazol-1-yl, 1-methyl-1H-tetrazol-5-yl, 2-methyl-2H-tetrazol-5-yl, etc.], pyridyl [e.g. 4-methylpyridin-3-yl, etc.], pyrimidinyl [e.g. 5-methylpyrimidin-2-yl, etc.], pyrazinyl [e.g. 5-methylpyrazin-2-yl, etc.], pyridazinyl [e.g. 6-methylpyridazin-3-yl, etc, ], 2,4-diamino-1,3,5-triazin-6-yl, 5-methyl-2-oxo-benzothiazolin-3-yl, or the like.

Suitable examples of the acid residue for X may be halide [e.g. chloride, bromide, iodide, etc.], sulfonate [e.g. benzenesulfonate, tosylate, etc.] or the like. A suitable subdefinition of the substituents $R^1$, $R^2$ and $R^3$ is as follows: $R^1$ is hydrogen, $R^2$ is ar(lower) alkyl which may be substituted with halogen, or aryl which may be substituted with lower alkoxy or halogen, and $R^3$ is pyridyl or imidazolyl optionally substituted with lower alkyl.

Suitable pharmaceutically acceptable salts of the object compounds (I) are conventional non-toxic salts and include an organic acid salt [e.g. formate, acetate, trifluoroacetate, maleate, fumarate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine salt, glutamic acid salt, ornithine salt, etc.] or the like.

The processes for preparing the object compounds (I) and salts thereof are explained in detail in the following.

Process 1

The object compound (I) and its salt can be prepared by reacting a compound (II) or its salt with a compound (III) or its salt.

Suitable salts of the compounds (II) and (III) may be the same as those exemplified for the compound (I).

This reaction is usually carried out in the presence of a base.

Suitable base may include an inorganic base such as alkali metal hydride [e.g. sodium hydride, potassium hydride, etc.], alkali metal hydroxide [e.g. sodium hydroxide, potassium hydroxide, etc.], alkaline earth metal hydroxide [e.g. magnesium hydroxide, calcium hydroxide, etc.], alkali metal carbonate [e.g. sodium carbonate, potassium carbonate, etc.], alkaline earth metal carbonate [e.g. magnesium carbonate, calcium carbonate, etc.], alkali metal bicarbonate [e.g. sodium bicarbonate, potassium bicarbonate, etc.], alkali metal acetate [e.g. sodium acetate, potassium acetate, etc.], alkaline earth metal phosphate [e.g. magnesium phosphate, calcium phosphate, etc.], alkali metal hydrogen phosphate [e.g. disodium hydrogen phosphate, dipotassium hydrogen phosphate, etc.], and an organic base such as trialkylamine [e.g. trimethylamine, triethylamine, etc.], picoline, N-methylpyrrolidine, N-methylmorpholine. And further, compound (III) per se can also be used as a base.

This reaction is usually carried out in a solvent such as alcohol [e.g. methanol, ethanol, etc.], benzene, N,N-dimethylformamide, tetrahydrofuran, diethyl ether or any other solvent which does not adversely affect the reaction.

The reaction temperature is not critical and the reaction is usually carried out at ambient temperature, or under warming or heating.

In case that the compound (II) possesses two or more reactive sites in the molecule, this reaction is preferably carried out by the following steps in order to increase the selectivity of the reactive site.
(1) reacting a compound (II) or its salt with a compound (III) protected by a conventional protective group [e.g. formyl, acetyl, etc.] at one or more reactive site(s) or its salt,
(2) eliminating the protective group(s) of the reaction product by a conventional manner [e.g. hydrolysis, etc.].

This method can be carried out according to Example mentioned later or analogous method thereto, and this method is also included within the scope of Process 1.

Process 2

The object compound (I) and its salt can be prepared by cyclizing the compound (IV) or its salt.

Suitable salts of the compound (IV) may be the same as those exemplified for the compound (I).

This reaction may be preferably carried out in the presence of an acid such as inorganic acid [e.g. hydrochloric acid, sulfuric acid, polyphosphoric acid, etc.], organic acid [e.g. trifluoroacetic acid, benzenesulfonic acid, toluenesulfonic acid, etc.] or the like.

This reaction can be carried out in the absence or presence of a conventional solvent such as aromatic hydrocarbon [e.g. benzene, toluene, xylene, etc.], alcohol [e.g. methanol, ethanol, propanol, isopropyl alcohol, butanol, tert-butyl alcohol, etc.] or any other organic solvent which does not adversely influence the reaction. In case that the acid to be used is liquid, it can also be used as a solvent.

This reaction is preferably carried out under dehydrating condition such as an azeotropic dehydration, in the presence of a dehydrating agent [e.g. anhydrous magnesium sulfate, anhydrous zinc chloride, phosphorus pentoxide, zeolite, silica gel, etc.], or the like.

The reaction temperature is not critical, and the reaction is usually carried out under warming or heating.

Process 3

The object compound (Ia) and its salt can be prepared by reacting a compound (V) or its salt with dicyanodiamide or its salt or an azide compound.

Suitable salts of dicyanodiamide may be the same as those exemplified for the compound (I).

Suitable example of the azide compound may be an inorganic base salt of azide [e.g. sodium azide, potassium azide, lithium azide, calcium azide, barium azide, etc.], hydrogen azide, hydrazonic acid, ammonium azide or the like.

This reaction is usually carried out in a conventional solvent which does not adversely influence the reaction such as water, methanol, ethanol, dioxane, N,N-dimethylformamide, methyl cellosolve, ethyl cellosolve or a mixture thereof.

The reaction temperature is not critical, and the reaction is usually carried out at ambient temperature or under warming or heating.

Among the starting compounds (II) and (IV), the new compounds can be prepared by the following processes.

Process A

X—A—COOH (VII)
or its reactive derivative at the carboxy group or a salt thereof

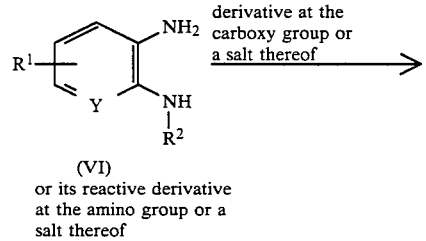

(VI)
or its reactive derivative at the amino group or a salt thereof

-continued

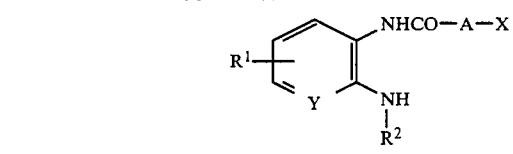

(VIII)
or its salt cyclizaion

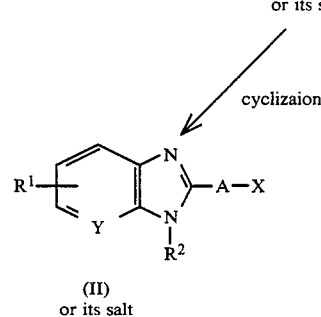

(II)
or its salt

Process B $R^3$—A—COOH (IX)
or its reactive derivative at the carboxy group or a salt thereof

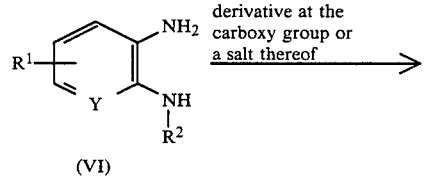

(VI)
or its reactive derivative at the amino group or a salt thereof

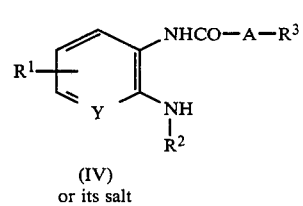

(IV)
or its salt

In the above formulas, $R^1$, $R^2$, $R^3$, A, Y and X are each defined above.

The processes for preparing the starting compounds (II) and (IV) and salts thereof are explained in detail in the following.

Process A (i) Preparation of the compound (VIII) (Step 1):

The compound (VIII) and its salts can be prepared by reacting a compound (VI) or its reactive derivative at the amino group or a salt thereof with a compound (VII) or its reactive derivative at the carboxy group or a salt thereof.

Suitable salts of the compound (VI) may be the same as those exemplified for the compound (I), and suitable salts of the compound (VII) may be a conventional organic or inorganic base addition salt [e.g. sodium salt, potassium salt, triethylamine salt, etc.].

Suitable reactive derivatives at the amino group of the compound (VI) include conventional ones used in amidation, for example, Schiff's base type imino or its tautomeric enamine type isomer formed by reaction of the compound (VI) with a carbonyl compound, a silyl derivative formed by reaction of the compound (VI) with a silyl compound such as trimethylsilylacetamide, bis(trimethylsilyl)acetamide or the like, a derivative formed by reaction of the compound (VI) with phosphorus trichloride or phosgene, and the like.

Suitable reactive derivative at the carboxy group of the compound (VII) may include an acid halide, an acid anhydride, an ester, an activated amide, an activated ester and the like.

Suitable examples of such reactive derivatives may be an ester such as lower alkyl ester [e.g. methyl ester, ethyl ester, propyl ester, hexyl ester, etc.], acid chloride, an acid azide, a mixed acid annydride with an acid such as substituted phosphoric acid [e.g. dialkylphosphoric acid, phenylphosphoric acid, etc.], aliphatic carboxylic acid [e.g. pivalic acid, acetic acid, trichloroacetic acid, etc.] or the like a symmetrical acid anhydride, an activated amide with imidazole, triazole or dimethylpyrazole, an activated ester with N-hydroxysuccinimide, N-hydroxyphthalimide or 1-hydroxy-6-chlorobenzotriazole, and the like.

The reactive derivatives of the compounds (VI) and (VII) can be selected according to the kinds of the compounds (VI) and (VII), respectively.

When the compound (VII) is used in a free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, phosphorus oxychloride, phosphorus oxybromide, oxalyl chloride, lower alkoxycarbonyl halide e.g. ethyl chloroformate, isobutyl chloroformate, etc.], 1-(p-chlorobenzenesulfonyloxy)-6-chloro-1H-benzotriazole, or the like.

The reaction is usually carried out in a conventional solvent such as water, acetone, dioxane, chloroform, methylene chloride, ethylene chloride, tetrahydrofuran, ethyl acetate, N,N-dimethylformamide, pyridine or any other organic solvent which does not adversely influence the reaction. Among these solvents, hydrophilic solvents may be used in a mixture with water.

The reaction may be preferably carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], tri(lower)alkylamine [e.g. trimethylamine, triethylamine, etc.], pyridine or its derivative [e.g. picoline, lutidine, 4-dimethylaminopyridine, etc.], or the like. In case that the base or the condensing agent to be used is liquid, it can also be used as a solvent.

The reaction temperature is not critical, and the reaction can be carried out under cooling, at ambient temperature or under warming or heating.

(ii) Preparation of the compound (II) (Step 2):

The compound (II) and its salt can be prepared by cyclizing a compound (VIII) or its salt.

This reaction can be carried out substantially in the same manner as Process 2, and therefore the reaction mode and reaction conditions [e.g. acid, dehydrating agent, solvent, reaction temperature, etc.] of this reaction are to be referred to those as explained in Process 2.

Process B

The compound (IV) and its salt can be prepared by reacting a compound (VI) or its reactive derivative at the amino group or a salt thereof with a compound (IX) or its reactive derivative at the carboxy group or a salt thereof.

Suitable salts of the compound (VI) may be the same as those exemplified for the compound (I), and suitable salts of the compound (IX) may be a conventional organic or inorganic base addition salt [e.g. sodium salt, potassium salt, triethylamine salt, etc.].

This reaction can be carried out substantially in the same manner as that of Step 1 of Process A, and therefore the reaction mode and reaction conditions [e.g. reactive derivatives, condensing agent, solvent, reaction temperature, etc.] of this reaction are to be referred to those as explained in Step 1 of Process A.

The reaction product can be used in the next step (i.e. Process 2) with or without isolation. The isolation can be carried out by a conventional manner.

It is to be noted that each of the object compound (I) and the starting compounds (II), (IV) and (V) include one or more stereoisomers due to asymmetric carbon atoms in the molecule, and all of such isomers of the compounds (I), (II), (IV) and (V) are included within the scope of this invention.

The object compounds (I) and their pharmaceutically acceptable salts of the present invention are novel and exhibit high inhibitory activity on ulcer.

In order to illustrate the usefulness of the object compound (I), the pharmacological data of some of the object compounds (I) are shown in the following.

(A) Inhibition on Ethanol Ulcer

Test Method :

Five male Sprague-Dawley rats, aged 7 weeks and weighing about 200 g, were used per group for the study on ethanol ulcer after the fast for 24 hours.

Test compound was suspended in 0.1% methylcellulose aqueous solution, and the suspension (5 ml/kg) was orally given to each rat.

The control group was given a vehicle, i.e. 0.1% methylcellulose aqueous solution (5 ml/kg), alone in the same way.

Absolute ethanol (5 ml/kg) was orally administered 30 minutes after dosing with test compound, and one hour later, the rats were sacrificed and their stomachs were removed. The area of ulcers of each rat was measured. The mean area ($mm^2$) in the medicated group was compared with that in the control group.

Test Result:

Test Compound:2-(Imidazol-1-yl)methyl-1-phenyl-1H-benzimidazole

The $ED_{50}$ value of the test compound:3.4 mg/kg (B) Inhibition on Stress Ulcer Test Method:

Five Sprague-Dawley rats weighing about 200 g were used per group. Each animal was immobilized in a small cage and put in a water bath allowing to respire. The temperature of the water bath kept at 22° C. The test compound was administered orally just before the immobilization. Seven hours later, the animals were sacrificed and their stomachs were removed. The stomach was then fixed with 2% formalin. The area of ulcers was measured for each animal. The mean area ($mm^2$) in the medicated animals was compared with that in the control animals.

Test Result:

Test Compound:2-(Imidazol-1-yl)methyl-1-phenyl-1H-benzimidazole

The ED$_{50}$ value of the test compound: 7.9 mg/kg (C) Gastric Secretion in Heidenhain Pouch Dogs Test Method:

Beagle dogs, weighing about 8–13 kg, were used for the study on gastric secretion. The animals were surgically provided with a vagally denervated Heidenhain pouch. One month or more later, the dogs were fasted overnight. Gastric secretion was stimulated by an intravenous infusion of tetragastrin (10 μg/kg/hr). Gastric samples were collected at 15 min intervals. After its volume was almost constant, test compound suspended in 0.1% methylcellulose solution was injected intravenously (0.2 ml/kg). Acid concentration was determined by tritrating an aliquot to pH 7.0 with 0.1 N sodium hydroxide solution using automatic titration (Hiranuma RAT-11 Type). Total acid output was calculated by multiplying total volume of gastric samples by acid concentration, and percentage change of total acid output was calculated by comparing with predosing value of test compound.

Test Result:

Test Compound:2-(Pyridin-3-yl)methyl-1-phenyl-1H-benzimidazole

The inhibition of the test compound (Dose: 1 mg/kg, iv): 92.9%

As being apparent from the above test results, the object compounds [I] of the present invention are useful as antiulcer medicines.

For therapeutic purpose, the compounds according to the present invention can be used in a form of pharmaceutical preparation containing said compound as an active ingredient, in admixture with a pharmaceutically acceptable carrier such as an organic or inorganic solid or liquid excipient suitable for oral or parenteral administration. The pharmaceutical preparations may be capsules, tablets, dragees, solution, suspension, emulsion, and the like. If desired, there may be included in the above preparations auxiliary substances, stabilizing agents, wetting or emulsifying agents, buffers and other commonly used additives.

While the dosage of the compounds will vary depend upon the age and condition of the patient, an average single dose of about 5 mg, 10 mg, 50 mg, 100 mg, 250 mg, 500 mg, and 1000 mg of the compounds according to the present invention may be effective for treating ulcer. In general, amounts between 1 mg/body and about 6,000 mg/body or even more may be administered per day.

The following preparations and examples are given for the purpose of illustrating the present invention.

PREPARATION 1

To a solution of 2-anilinoaniline (4.0 g) in a mixture of dichloromethane (20 ml) and pyridine (6.87 g) was dropwise added 4-chlorobutyryl chloride (4.29 g) at 8° C. during a period of 16 minutes. The mixture was stirred at the same temperature for 40 minutes and then diluted with ice-water. The mixture was extracted twice with dichloromethane. The combined extract was washed with 1 N hydrochloric acid and water in turn and dried over magnesium sulfate. The solvent was removed under reduced pressure to give a crystalline residue of 4-chloro-N-(2-anilinophenyl)butyramide (4.3 g).

IR (Nujol) : 3350, 3200, 1635, 1585 cm$^{-1}$.

NMR (CDCl$_3$, δ) : 1.8–2.65 (4H, m), 3.57 (2H, t, J=6 Hz), 5.63 (1H, m), 6.67–8.17 (10H, m).

PREPARATION 2

2-Chloro-N-(2-anilinophenyl)propanamide was obtained according to substantially the same manner as that of Preparation 1.

mp 73°–78° C.

IR (Film) : 3350, 1670, 1610 cm$^{-1}$.

NMR (CDCl$_3$, δ) : 1.7 (3H, d, J=7 Hz), 4.45 (1H, q, J=7 Hz), 4.8 (1H, m), 6.65–7.5 (8H, m), 7.8–8.15 (1H, m), 8.7 (1H, m).

PREPARATION 3

2-Chloro-N-[2-(3-methylanilino)phenyl]acetamide was obtained according to substantially the same manner as that of Preparation 1.

mp 112–113° C.

IR (Nujol) : 3350, 3315, 1670, 1595 cm$^{-1}$.

NMR (CDCl$_3$, δ) : 2.27 (3H, s), 4.1 (2H, s), 5.4 (1H, m), 6.37–7.4 (7H, m), 7.8–8.2 (1H, m), 8.65 (1H, m).

PREPARATION 4

2-Chloro-N-[2-(4-methoxyanilino)phenyl]acetamide was obtained according to substantially the same manner as that of Preparation 1.

mp 93°–94° C.

IR (Nujol) 3325, 3220, 1640, 1600 cm$^{-1}$.

NMR (CDCl$_3$, δ) : 3.75 (3H, s), 4.12 (2H, s), 5.4 (1H, m), 6.8–7.3 (7H, m), 7.7–8.05 (1H, m), 8.65 (1H, m).

PREPARATION 5

2-Chloro-N-[2-(4-chloroanilino)phenyl]acetamide was obtained according to substantially the same manner as that of Preparation 1.

mp 96°–97° C.

IR (Nujol) 3360, 3250, 1660, 1605 cm$^{-1}$.

NMR (CCl$_4$, δ) : 4.02 (2H, s), 5.65 (1H, m), 6.55–7.28 (7H, m), 7.65–8.02 (1H, m), 8.55 (1H, m).

PREPARATION 6

2-Chloro-N-(5-methoxy-2-anilinophenyl)acetamide was obtained according to substantially the same manner as that of Preparation 1.

mp 94°–95° C.

IR (Nujol) : 3380, 3340, 1665, 1585 cm$^{-1}$.

NMR (CDCl$_3$, δ) : 3.8 (3H, s), 4.03 (2H, s), 5.1 (1H, m), 6.45–7.4 (7H, m), 7.93 (1H, d, J=3 Hz), 8.97 (1H, m)

PREPARATION 7

A solution of 2-chloro-N-(2-anilinophenyl)acetamide (10 g) and p-toluenesulfonic acid monohydrate (4.5 g) in benzene (250 ml) was refluxed for 1.5 hours under an azeotropic dehydration. After being cooled to ambient temperature, the reaction mixture was diluted with an aqueous sodium bicarbonate solution and extracted with ethyl acetate three times. The combined organic layer was washed successively with water and brine, dried over anhydrous magnesium sulfate and evaporated under reduced pressure. The residual oil was purified by column chromatography on silica gel (100 g) with dichloromethane as an eluent to afford 2-chloromethyl-1-phenyl-1H-benzimidazole (3.4 g).

mp 117°–119° C.

IR (Nujol) 1610, 1592, 1495 cm$^{-1}$.

NMR (DMSO-d$_6$, δ) : 4.64 (2H, s), 7.0–7.9 (9H, m).

PREPARATION 8

2-(1-Chloroethyl)-1-phenyl-1H-benzimidazole was obtained according to substantially the same manner as that of Preparation 7.

mp 71°–72° C.

IR (Nujol) : 1600, 1585, 1490 cm$^{-1}$.

NMR (CCl$_4$, δ) : 2.03 (3H, d, J=7 Hz), 4.95 (1H, q, J=7 Hz), 6.85–7.9 (9H, m).

PREPARATION 9

2-Chloromethyl-1-(3-methylphenyl)-1H-benzimidazole was obtained according to substantially the same manner as that of Preparation 7.

IR (Film) : 1600, 1585, 1510 cm$^{-1}$.

NMR (CDCl$_3$, δ) : 2.47 (3H, s), 4.7 (2H, s), 7.07–8.07 (8H, m).

PREPARATION 10

2-Chloromethyl-1-(4-methoxyphenyl)-1H-benzimidazole was obtained according to substantially the same manner as that of Preparation 7.

mp 131°–133° C.

IR (Nujol) 1610, 1585, 1515, 1460 cm$^{-1}$.

NMR (CDCl$_3$, δ) : 3.9 (3H, s , 4.63 (2H, s), 6.95–8.0 (8H, m).

PREPARATION 11

2-Chloromethyl-1-(4-chlorophenyl)-1H-benzimidazole was obtained according to substantially the same manner as that of Preparation 7.

mp 126°–127° C.

IR (Nujol) : 1615, 1590, 1495 cm$^{-1}$.

NMR (CDCl$_3$, δ) : 4.67 (2H, s), 6.9–7.95 (8H, m).

PREPARATION 12

2-Chloromethyl-5-methoxy-1-phenyl-1H-benzimidazole was obtained according to substantially the same manner as that of Preparation 7.

mp 121°–123° C.

IR (Nujol) 1620, 1580, 1495 cm$^{-1}$.

NMR (CDCl$_3$, δ) : 3.85 (3H, s), 4.65 (2H, s), 6.7–7.73 (8H, m).

PREPARATION 13

A solution of 4-chloro-N-(2-anilinophenyl)butyramide (0.5 g) and p-toluenesulfonic acid monohydrate (33 mg) in toluene (15 ml) was refluxed for 1.5 hours. Toluene was removed under reduced pressure to afford a residue, which was dissolved in dichloromethane (20 ml), washed with a saturated aqueous solution of sodium bicarbonate and water in turn and dried over magnesium sulfate. Removal of the solvent under reduced pressure afforded an oily residue, which was subjected to column chromatography on silica gel (5 g) eluting with a mixture of dichloromethane and ethyl acetate (10:1) to give crystals of 2-(3-chloropropyl)-1-phenyl-1H-benzimidazole (148 mg).

mp 71°–72° C.

IR (Nujol) : 1610, 1595, 1510, 1500 cm$^{-1}$.

NMR (CDCl$_3$, δ) : 1.85–2.7 (2H, m), 2.95 (2H, t, J=6 Hz), 3.5–4.0 (2H, m), 7.0–7.9 (9H, m).

Mass: 270 (M+).

The second fraction was combined and evaporated to give crystals of 2-(3-hydroxypropyl)-1-phenyl-1H-benzimidazole (128 mg).

mp 94°–95° C.

IR (Nujol) : 3300, 1610, 1595, 1500 cm$^{-1}$.

NMR (CDCl$_3$, δ) : 1.85–2.7 (2H, m), 2.8–3.2 (2H, m), 3.5–3.9 (2H, m), 7.0–8.0 (9H, m)

Mass : 252 (M+).

PREPARATION 14

A solution of 2-(3-hydroxypropyl)-1-phenyl-1H-benzimidazole (1.15 g) and thionyl chloride (0.6 g) in chloroform (23 ml) was refluxed for 1.5 hours. After being cooled, the mixture was diluted with a saturated aqueous solution of sodium bicarbonate. The chloroform layer was washed with water and a saturated aqueous solution of sodium chloride in turn, and dried over magnesium sulfate. The solvent was evaporated under reduced pressure to afford 2-(3-chloropropyl)-1-phenyl-1H-benzimidazole (1.0 g).

IR (Nujol) : 1610, 1595, 1510, 1500 cm$^{-1}$.

PREPARATION 15

To a mixture of 3-amino-2-anilinopyridine (0.5 g), 2-(imidazol-1-yl)acetic acid (0.38 g) and pyridine (0.24 ml) in chloroform (5 ml) was dropwise added phosphorus oxychloride (0.28 ml) and the mixture was refluxed for 1.5 hours. After being cooled, the reaction mixture was decanted and the residue was poured into saturated aqueous sodium bicarbonate. The mixture was extracted three times with ethyl acetate. The combined extract was dried over magnesiumsulfate and the solvent was evaporated under reduced pressure. The resultant residue was triturated in ethyl acetate (10 ml) to give 2-(imidazol-1-yl)-N-(2-anilinopyridin 3-yl)acetamide (200 mg).

mp 151°–154° C.

IR (Nujol) : 3350, 1700, 1640, 1610 cm$^{-1}$.

NMR (DMSO-d$_6$, δ) : 4.95 (2H, s), 6.7–8.3 (12H, m), 9.73 (1H, brs).

Mass : 293 (M+).

EXAMPLE 1

A solution of 2-chloromethyl-1-phenyl-1H-benzimidazole (3.4 g) and imidazole (4.8 g) in ethanol (25 ml) was stirred at 60° C for 7 hours. The reaction mixture was concentrated under reduced pressure to give an oil, which was diluted with water and extracted three times with dichloromethane. The combined extract was washed twice with water and once with brine, dried over anhydrous magnesium sulfate and evaporated under reduced pressure. The residue was purified by column chromatography on silica gel (100 g) with a mixture of methanol and dichloromethane (3:97) as an eluent to afford an oil, which was crystallized from a mixture of ethyl acetate and hexane to give 2-(imidazol-1-yl)methyl-1-phenyl-1H-benzimidazole (2.65 g).

mp. 116°–117° C.

IR (Nujol) : 1612, 1590, 1495 cm$^{-1}$.

NMR (DMSO-d$_6$, δ) : 5.40 (2H, s), 6.8–7.8 (12H, m)

Analysis: Calcd. for C$_{17}$H$_{14}$N$_4$: Calcd.: C 74.43, H 5.14, N 20.43; Found : C 73.84, H 5.14, N 20.25.

EXAMPLE 2

A solution of 2-chloromethyl-1H-benzimidazole (4.85 g) and imidazole (9.9 g) in ethanol (37 ml) was stirred at 70° C. for 6 hours. The reaction mixture was concentrated under reduced pressure. The residue was purified by column chromatography on silica gel (120 g) with a mixture of methanol and dichloromethane (5:95) as an eluent to afford an oil, which was crystallized from ethyl acetate. Recrystallization from a mixture of methanol and diethyl ether to give 2-(imidazol-1-yl)methyl-1H-benzimidazole (0.76 g).

mp. 198°-200° C.

IR (Nujol) : 3100, 1660, 1620, 1515 cm$^{-1}$.

NMR (DMSO-d$_6$, δ) : 5.14 (2H, s), 6.86 (1H, s), 7.0–7.64 (6H, m), 7.76 (1H, s).

Analysis: Calcd. for C$_{11}$H$_{10}$N$_4$: Calcd.:C 66.65, H 5.09, N 28.51; Found :C 66.66, H 5.05, N 28.51.

EXAMPLE 3

A solution of 2-chloromethyl-1-(4-chlorobenzyl)-1H-benzimidazole (2.0 g) and imidazole (2.34 g) in acetonitrile (20 ml) was heated at 90° C. for 1.5 hours. The reaction mixture was concentrated under reduced pressure to give an oil, which was diluted with water and extracted three times with ethyl acetate. The combined extract was washed twice with water, dried over anhydrous magnesium sulfate and concentrated under reduced pressure. The residue was purified by column chromatography on silica gel (30 g) with a mixture of methanol and dichloromethane (10:90) as an eluent to give an oil (1.6 g). To a solution of the oil in methanol (20 ml) was added fumaric acid (0.59 g). The mixture was filtered to remove an insoluble material and the filtrate was evaporated under reduced pressure to give a crystalline residue, which was recrystallized from methanol to afford pure 2-(imidazol-1-yl)methyl-1-(4-chlorobenzyl)-1H-benzimidazole fumarate (1.6 g).

mp. 162°-163° C.

IR (Nujol) : 1690, 1635, 1600, 1515, 1495 cm$^{-1}$.

NMR (DMSO-d$_6$, δ) : 5.67 (4H, s), 6.67 (2H, s), 7.0–7.8 (10H, m), 7.93 (1H, brs), 9.53 (2H, brs)

Analysis: Calcd. for C$_{22}$H$_{19}$ClN$_4$O$_4$: Calcd.: C 60.21, H 4.36, N 12.77; Found : C 59.65, H 4.37, N 12.78.

EXAMPLE 4

To a solution of imidazole (226 mg) in N,N-dimethylformamide (9 ml) was added sodium hydride (60% in oil, 140 mg) with stirring and ice-cooling. The mixture was stirred for 15 minutes at the same temperature and for 1 hour at 100° C. To the resultant mixture, after cooling, was added 2-(3-chloropropyl)-1-phenyl-1H-benzimidazole (0.9 g) and the mixture was stirred for 1 hour at 100° C. After being cooled, the reaction mixture was diluted with water and extracted with dichloromethane. The combined extract was washed with water and saturated aqueous sodium chloride in turn, and dried over magnesium sulfate. The solvent was removed under reduced pressure to give an oily residue, which was subjected to column chromatography on silica gel (9 g) eluting with a mixture of dichloromethane and methanol (50:1) to give an oil. To a solution of the oil in diethyl ether (30 ml) was added a solution of oxalic acid dihydrate (321 mg) in ethanol to give an oily precipitate. The oily precipitate was triturated in ethanol to give powder of 2-[3-(imidazol-1-yl)propyl]-1-phenyl-1H-benzimidazole oxalate (920 mg).

mp. 141°-143° C.

IR (Nujol) : 1610, 1590, 1500, 1210 cm$^{-1}$.

NMR (DMSO-d$_6$, δ) : 2.0–3.0 (4H, m), 4.25 (2H, t, J=6.5 Hz), 7.0–7.9 (11H, m), 8.6 (1H, s).

Analysis: Calcd. for C$_{19}$H$_{18}$N$_4$. C$_2$H$_2$O$_4$: Calcd.: C 64.28, H 5.14, N 14.28; Found : C 64.37, H 5.19, N 14.31.

EXAMPLE 5

To a solution of sodium ethoxide, prepared from sodium metal (230 mg) and ethanol (24 ml), were added H-1,2,4-triazole (690 mg) and 2-chloromethyl-1-phenyl-1H-benzimidazole (2.4 g) with stirring at ambient temperature. The mixture was refluxed for 1.5 hours and evaporated under reduced pressure. The resultant residue was subjected to column chromatography on silica gel (50 g) eluting with a mixture of chloroform and methanol (200:3) to give a crystalline product. The crystal was recrystallized from isopropyl alcohol to give 2-(1H-1,2,4-triazol-1-yl)methyl-1-phenyl-1H-benzimidazole (1.65 g).

mp. 154°-156° C.

IR (Nujol) : 1595, 1500, 1450 cm$^{-1}$.

NMR (CDCl$_3$, δ) : 5.5 (2H, s), 7.0–8.0 (9H, m), 7.83 (1H, s), 8.05 (1H, s).

Analysis: Calcd. for C$_{16}$H$_{13}$N$_5$: Calcd.: C 69.80, H 4.76, N 25.44; Found : C 69.77, H 4.93, N 25.22.

EXAMPLE 6

2-(4-Methylimidazol-1-yl)methyl-1-phenyl-1H-benzimidazole.mono oxalate.½hydrate was obtained according to substantially the same manner as that of Example 1.

mp. 137°-138° C.

IR (Nujol) : 1720, 1630, 1600, 1500 cm$^{-1}$.

NMR (DMSO-d$_6$, δ) : 2.2 (3H, s), 5.62 (2H, s), 7.0–7.9 (10H, m), 8.3 (1H, s), 9.25 (2H, s)

Analysis: Calcd. for C$_{18}$H$_{16}$N$_4$.C$_2$H$_2$O$_4$.½H$_2$O: Calcd.: C 62.00, H 4.94, N 14.46; Found : C 62.53, H 5.05, N 14.25.

EXAMPLE 7

2-(2-Methylimidazol-1-yl)methyl-1-phenyl-1H-benzimidazole was obtained according to substantially the same manner as that of Example 1.

mp. 124°-126° C.

IR (Nujol) : 1610, 1595, 1500 cm$^{-1}$.

NMR (CDCl$_3$, δ) : 2.0 (3H, s), 5.15 (2H, s), 6.6 (1H, d, J=2 Hz), 6.8 (1H, d, J=2 Hz), 6.9–8.0 (9H, m).

Analysis: Calcd. for C$_{18}$H$_{16}$N$_4$: Calcd. : C 74.98, H 5.59, N 19.43; Found : C 75.07, H 5.71, N 19.47.

EXAMPLE 8

2-[1-(Imidazol-1-yl)ethyl]-1-phenyl-1H-benzimidazole dihydrochloride.½hydrate was obtained according to substantially the same manner as that of Example 1.

mp. 175°-190° C.

IR (Nujol) : 3350, 2550, 2495, 1580, 1545 cm$^{-1}$.

NMR (DMSO-d$_6$, δ) : 1.9 (3H, d, J=7 Hz), 6.18 (1H, q, J=7 Hz), 6.95–8.0 (11H, m), 9.17 (1H, m)

Analysis: Calcd. for C$_{18}$H$_{16}$N$_4$.2HCl.½H$_2$O: Calcd.: C 58.39, H 5.17, N 15.13; Found : C 58.12, H 5.42, N 14.88.

EXAMPLE 9

2-(Imidazol-1-yl)methyl-1-(3-methylphenyl)-1H-benzimidazole was obtained according to substantially the same manner as that of Example 1.

mp. 91°-93° C.

IR (Nujol) : 1603, 1590, 1518, 1502 cm$^{-1}$.

NMR (CDCl$_3$, δ) : 2.4 (3H, s), 5.25 (2H, s), 6.77–8.05 (11H, m).

Analysis: Calcd. for C$_{18}$H$_{16}$N$_4$; Calcd.: C 74.98, H 5.59, N 19.43; Found : C 74.73, H 5.60, N 19.41.

EXAMPLE 10

2-(Imidazol-1-yl)methyl-1-(4-methoxyphenyl)-1H-benzimidazole was obtained according to substantially the same manner as that of Example 1.

mp. 113°-114° C.

IR (Nujol) : 1612, 1585, 1512 cm$^{-1}$.
NMR (CDCl$_3$, δ) : 3.9 (3H, s), 5.25 (2H, s), 6.8–8.0 (11H m).
Analysis: Calcd. for C$_{18}$H$_{16}$N$_4$O: Calcd.: C 71.04, H 5.30, N 18.41; Found : C 71.06, H 5.38, N 18.39

EXAMPLE 11

1-(4-Chlorophenyl)-2-(imidazol-1-yl)methyl-1H-benzimidazole was obtained according to substantially the same manner as that of Example 1.
mp. 121°–122° C.
IR (Nujol) : 1607, 1490 cm$^{-1}$.
NMR (CDCl$_3$, δ) : 5.25 (2H, s), 6.75–8.0 (11H, m),
Analysis: Calcd. for C$_{17}$H$_{13}$ClN$_4$: Calcd.: C 66.13, H 4.24, N 18.15: Found : C 66.42, H 4.33, N 18.17.

EXAMPLE 12

2-(Imidazol-1-yl)methyl-5-methoxy-1-phenyl-1H-benzimidazole was obtained according to substantially the same manner as that of Example 1.
mp. 104°–106° C.
IR (Nujol) : 1620, 1597, 1500 cm$^{-1}$.
NMR (CDCl$_6$, δ) : 3.85 (3H, s), 5.23 (2H, s), 6.7–7.7 (11H, m).
Analysis: Calcd. for C$_{18}$H$_{16}$N$_4$O: Calcd.: C 71.04, H 5.30, N 18.41; Found : C 71.00, H 5.43, N 18.30.

EXAMPLE 13

2-(Imidazol-1-yl)methyl-1-methyl-1H-benzimidazole was obtained according to substantially the same manner as that of Example 1.
mp. 151°–152° C.
IR (Nujol) : 1618, 1590, 1510 cm$^{-1}$.
NMR (CDCl$_6$, δ) : 3.57 (3H, s), 5.35 (2H, s), 6.85–7.95 (7H, m).
Analysis: Calcd. for C$_{12}$H$_{12}$N$_4$: Calcd.: C 67.91, H 5.70, N 26.40; Found : C 68.34, H 5.80, N 26.42.

EXAMPLE 14

A mixture of 2-chloromethyl-1-phenyl-1H-benzimidazole (4.8 g) and 1-acetyl-4-methylimidazole (2.4 g) in acetonitrile (25 ml) was refluxed for 48 hours. After removal of the solvent, the residue was pulverized in diethyl ether to give powder, which was taken up in 2.5 N sodium hydroxide (20 ml) and refluxed for 15 minutes. The resultant mixture was extracted twice with chloroform. The combined organic layer was extracted twice with 1 N hydrochloric acid. The combined aqueous layer was adjusted to pH 8.0 with aqueous sodium bicarbonate and extracted twice with chloroform. The combined extract was washed with water, dried over magnesium sulfate and evaporated under reduced pressure. The resultant residue was subjected to column chromatogeaphy on silica gel (60 g) eluting with a mixture of chloroform and methanol (50:1) to give an oily product. The oily product was triturated twice in diethyl ether and then in the mixture of diethyl ether and isopropyl alcohol (2:1) to give powder of 2-(5-methylimidazol-1-yl)methyl-1-phenyl-1H-benzimidazole (0.65 g).
mp. 100°–102° C.
IR (Nujol) : 1610, 1595, 1570, 1500 cm$^{-1}$.
NMR (CDCl$_3$, δ) : 1.95 (3H, s), 5.15 (2H, s), 6.65 (1H, brs), 6.8–8.0 (10H, m).
Analysis: Calcd. for C$_{18}$H$_{16}$N$_4$: Calcd.: C 74.98, H 5.59, N 19.43; Found : C 74.86, H 5.67, N 19.28.

EXAMPLE 15

Heating of 2-(imidazol-1-yl)-N-(2-anilinopyridin-3)acetamide (150 mg) at 200° C. for 5 minutes afforded a crude cyclized product, which was recrystallized from a mixture of ethyl acetate and n-hexane to give 2-(imidazol-1-yl)methyl-3-phenyl-3H-imidazo[4,5-b]pyridine (116 mg).
IR (Nujol) : 1595, 1500 cm$^{-1}$.
NMR (CDCl$_3$, δ) : 5.3 (2H, s), 6.76–7.8 (9H, m), 8.15 (1H, dd, J=8 Hz, 2 Hz), 8.4 (1H, dd, J=6 Hz, 2 Hz).

EXAMPLE 16

To a solution of 2-anilinoaniline (1.84 g) and 3-pyridineacetic acid (1.37 g) in chloroform (20 ml) was dropwise added phosphorus oxychloride (1.53 g) and the mixture was refluxed for 6 hours. After removal of the solvent under reduced pressure, the resultant residue was poured into a saturated aqueous solution of sodium bicarbonate. The mixture was extracted twice with ethyl acetate. The combined extract was washed with water and a saturated aqueous solution of sodium chloride successively, and dried over magnesium sulfate. The solvent was removed under reduced pressure to give a crystalline product, which was recrystallized from a mixture of isopropyl alcohol and n-hexane (1:2) to give 2-(pyridin-3-yl)methyl-1-phenyl-1H-benzimidazole (1.0 g).
mp. 115°–116° C.
IR (Nujol) : 1615, 1595, 1575, 1500 cm$^{-1}$.
NMR (CDCl$_3$, δ) : 4.2 (2H, s), 6.9–8.0 (11H, m), 8.25 (1H, d, J=2 Hz), 8.45 (1H, dd, J=6 Hz, 2 Hz).
Analysis: Calcd. for C$_{19}$H$_{15}$N$_3$: Calcd.: C 79.98, H 5.30, N 14.73; Found : C 79.96, H 5.52, N 14.68.

EXAMPLE 17

2-(Pyridin-2-yl)methyl-1-phenyl-1H-benzimidazole was obtained according to substantially the same manner as that of Example 16.
mp. 106°–108° C.
IR (Nujol) : 1590, 1570, 1500 cm$^{-1}$.
NMR (CDCl$_3$, δ) : 4.4 (2H, s), 6.9–8.0 (12H, m), 8.3–8.6 (1H, m).
Mass: 285 (M+).

EXAMPLE 18

3-(1-Phenyl-1H-benzimidazol-2-yl)methyl-benzothiazolin-2-one was obtained according to substantially the same manner as that of Example 16.
mp. 196°–198° C.
IR (Nujol) : 1678, 1595, 1500 cm$^{-1}$.
NMR (CDCl$_3$, δ) : 5.4 (2H, s), 6.8–7.9 (13H, m).
Analysis: Calcd. for C$_{21}$H$_{15}$N$_3$OS: Calcd.: C 70.57, H 4.23, N 11.76; Found : C 70.62, H 4.38, N 11.77.

EXAMPLE 19

2-[2-(Imidazol-1-yl)ethyl]-1-phenyl-1H-benzimidazole monohydrate was obtained according to substantially the same manner as that of Example 16.
mp. 80°–84° C.
IR (Nujol) : 1610, 1595, 1500 cm$^{-1}$.
NMR (CDCl$_3$, δ) : 3.2 (2H, t, J=6 Hz), 4.5 (2H, t, J=6 Hz), 6.7–8.0 (12H, m).
Analysis: Calcd. for C$_{18}$H$_{16}$N$_4$.H$_2$O: Calcd.: C 70.57, H 5.92, N 18.29; Found : C 71.03, H 6.03, N 18.38.

EXAMPLE 20

To a solution of 3-amino-2-anilinopyridine (2.0 g) and 2-(imidazol-1-yl)acetic acid (1.56 g) in pyridine (20 ml) was dropwise added phosphorus oxychloride (1.91 g) and the mixture was refluxed for 30 minutes. The reaction mixture was poured into saturated aqueous sodium bicarbonate and extracted three times with ethyl acetate. The combined extract was washed with saturated aqueous sodium chloride and dried over magnesium sulfate. The solvent was removed under reduced pressure to give a residue, which was subjected to column chromatography on silica gel (20 g) eluting with a mixture of dichloromethane and ethanol. The fractions containing the desired compound were combined and evaporated in vacuo. The resultant crystal was recrystallized from a mixture of ethyl acetate and n-hexane to give 2-(imidazol-1-yl)methyl-3-phenyl-3H-imidazo[4,5-b]pyridine (0.8 g).

mp. 146°–148° C.
IR (Nujol) : 1595, 1500, 1430 cm$^{-1}$.
NMR (CDCl$_3$, δ) : 5.3 (2H, s), 6.76–7.8 (9H, m), 8.15 (1H, dd, J=8 Hz, 2 Hz), 8.4 (1H, dd, J=6 Hz, 2 Hz).
Analysis: Calcd. for C$_{16}$H$_{13}$N$_5$: Calcd.: C 69.80, H 4.76, N 25.44; Found : C 70.24, H 5.11, N 25.63.

EXAMPLE 21

A mixture of 2-cyanomethyl-1-phenyl-1H-benzimidazole (6.2 g), sodium azide (5.18 g) and ammonium chloride (4.27 g) in N,N-dimethylformamide (62 ml) was heated at 100° C. for 4 hours. The reaction mixture was poured into water (620 ml) and the aqueous mixture was adjusted to pH 9 with 1 N sodium hydroxide. After being washed with ethyl acetate, the aqueous layer was further adjusted to pH 4 with acetic acid and extracted twice with ethyl acetate. The combined extract was washed with water and saturated sodium chloride in turn and dried over magnesium sulfate. The solvent was removed under reduced pressure to give a residue, which was recrystallized from a mixture of methanol and diisopropyl ether to give 5-(1-phenyl-1H-benzimidazol-2-yl)methyl-1H-tetrazole (5.3 g).

mp. 185°–187° C. (dec.).
IR (Nujol) : 1595, 1570, 1500, 1465 cm$^{-1}$.
NMR (DMSO-d$_6$, δ) : 4.6 (2H, s), 7.1–7.9 (9H, m).
Analysis: Calcd. for C$_{15}$H$_{12}$N$_6$: Calcd.: C 65.21, H 4.38, N 30.42; Found : C 65.06, H 4.58, N 30.24.

EXAMPLE 22

A mixture of 2-cyanomethyl-1-phenyl-1H-benzimidazole (1.8 g), dicyanodiamide (785 mg) and potassium hydroxide (87 mg) in methyl cellosolve was refluxed for 2 hours. After the mixture was cooled, the resultant precipitates were filtered off and washed with water and methanol in turn to give 2,4-diamino-6-(1-phenyl-1H-benzimidazol-2-yl)methyl-1,3,5-triazine (1.8 g).

mp. 337°–340° C.
IR (Nujol) : 3300, 3100, 1665, 1635 cm$^{-1}$.
NMR (CF$_3$COOH, δ) : 4.8 (2H, brs), 7.2–8.2 (9H, m).
Analysis: Calcd. for C$_{17}$H$_{15}$N$_7$: Calcd.: C 64.34, H 4.76, N 30.90; Found : C 64.28, H 4.88, N 31.02.

What we claim is:

1. A compound of the formula:

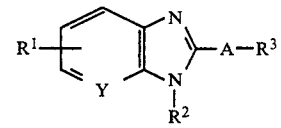

wherein
A is a lower alkylene,
R$^1$ is hydrogen, lower alkyl, lower alkoxy or halogen,
R$^2$ is cyclo (lower) alkyl, pyridyl, ar(lower)alkyl which may be substituted with halogen, or aryl which may be substituted with lower alkyl, lower alkoxy, hydroxy or halogen,
R$^3$ is a N-containing unsaturated heterocyclic group selected from imidazolyl, pyridyl, triazolyl, tetrazolyl, 1,3,5-triazinyl and 2-oxo-benzothiazolinyl, which may be substituted with lower alkyl or amino, and
Y is =C—, wherein ar and aryl are selected from phenyl and naphthyl, or a pharmaceutically acceptable salt thereof.

2. A compound of claim 1, wherein
R$^1$ is hydrogen or lower alkoxy, and
R$^2$ is ar(lower)alkyl which may be substituted with halogen, or aryl which may be substituted with lower alkyl, lower alkoxy or halogen.

3. A compound of claim 2, wherein
R$^1$ is hydrogen,
R$^2$ is ar(lower)alkyl which may be substituted with halogen, or aryl which may be substituted with lower alkoxy or halogen, and
R$^3$ is pyridyl or imidazolyl optionally substituted with lower alkyl.

4. A compound of claim 3, wherein
A is methylene,
R$^2$ is phenyl, and
R$^3$ is imidazolyl optionally substituted with lower alkyl.

5. A compound of claim 4, which is 2-(imidazol-1-yl)methyl-1-phenyl-1H-benezimidazole.

6. A pharmaceutical antiulcertive composition comprising an effective amount of a compound of claim 1, as an effective ingredient, in association with a pharmaceutically acceptable, substantially nontoxic carier or excipient.

7. A method for treatment of an ulcer which comprises administering an effective amount of compound of claim 1 to human beings or animals.

* * * * *